US006241987B1

(12) United States Patent
Lam

(10) Patent No.: US 6,241,987 B1
(45) Date of Patent: Jun. 5, 2001

(54) DIETARY SUPPLEMENT CONTAINING SAW PALMETTO, PUMPKIN SEED, AND NETTLE ROOT

(75) Inventor: Thanh Kevin Lam, Monterey Park, CA (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/259,857

(22) Filed: Mar. 1, 1999

Related U.S. Application Data

(63) Continuation-in-part of application No. 09/137,473, filed on Aug. 20, 1998.
(51) Int. Cl.$^7$ .............................. A61K 35/78; A61K 9/48; A23L 1/30
(52) U.S. Cl. ...................... 424/195.1; 424/451; 426/648
(58) Field of Search ................................ 424/195.1, 451; 426/648, 73, 655

(56) References Cited

U.S. PATENT DOCUMENTS

| | | | | |
|---|---|---|---|---|
| 4,886,665 | * | 12/1989 | Kovacs | 424/195.1 |
| 5,002,939 | * | 3/1991 | Steber | 514/173 |
| 5,264,428 | * | 11/1993 | Streber | 514/177 |
| 5,543,146 | * | 8/1996 | Perez | 424/195.1 |
| 5,547,673 | * | 8/1996 | Bombardelli | 424/195.1 |
| 5,565,214 | * | 10/1996 | Zambo et al. | 424/456 |
| 5,580,857 | * | 12/1996 | Oden | 514/25 |

OTHER PUBLICATIONS

Tyler, V. Herbs of Choice, Pharmaceutical Products Press, pp. 81–86, 1994.*
Blumenthal et al. The Complete German Commission E Monographs, pp. 193, 201, and 217, 1998.*
Product Alert Bulletin—Oct. 5, 1992, see abstract.*
E. Koch and A. Biber, "Pharmacological Effects of Saw Palmetto and Urtica Extracts for Benign Prostatic Hyperplasia". Urologe (1994), 34(2): 90–95.
W. Vahlensieck, et al. "Benign Prostatic Hyperplasia: Treatment with Sabal Fruit Extract. Observational study on 1334 patients". Fortschritte der Therapy (1993), 111:323–326, English summary on p. 326.
J. Braeckman, "The extract of Serenoa Repens in the Treatment of Benign Prostatic Hyperplasia; a multicenter open study". Current Therapeutic Research (1994), 55(7); 776–785.

B.E. Carbin et al. "Treatment of Benign Prostatic Hyperplasia with Phytosterols". British Journal of Urology (1990), 66:639–641.
M. Krieg, et al.. "Effect of Aging on Endogenous Level of 5a–Dihydrotestosterone, Testosterone, Estradiol, and Estrone in Epithelium and Stroma of Normal and Hyperplastic Human Prostate". Journal of Clinical Endocrinology (1993), 77(2):375–381.
N.G. Bisset,"Herbal Drugs and Phytopharmace Uticals" Medpharm GmbH Scientific Publishers (1994), pp. 508–509. (nettle root); pp. 170–172 (pumpkin seed).
H.J. Schneider, et al. "Treatment of Benign Prostatic Hyperplasia: Results of a surveilance study in practices of urological specialists using a combined plant–based preparation (Sabal extract WS 1473 and Urtica extract WS 1031)". (1995) Fortschr Med., 11(3): 37–40. (abstract only).
D. Brown, "Efficacy of Saw Palmetto/Urtica Root in the Treatment of BPH", Quarterly Review of Natural Medicine (Winter 1995), pp. 279–280.
W. Breu, et al. "Der Sabalfrucht–Extrakt SG 291"., Zeitschrift fur Phytotherapie 13 (1992), pp. 107–115 (English abstract p. 115).
T.J. Wilt, et al. "Saw Palmetto Extracts for Treatment of Benign Prostatic Hyperplasia", Quarterly Review of Natural Medicine (Winter 1995), pp. 279–280.
L. Rhodes,et al. "Comparison of Finasteride (Proscar®), a 5a Reductase Inhibitor, and Various Commercial Plant Extracts in In Vitro and In Vivo 5a Reductase Inhibition". The Prostate (1993), 22:43–51.

* cited by examiner

Primary Examiner—Christopher R. Tate
(74) Attorney, Agent, or Firm—Amway Corporation

(57) ABSTRACT

A dietary supplement and method for supporting and maintaining normal prostrate gland function is described. The dietary supplement of the present invention provides a unique combination of herbal extracts including saw palmetto, pumpkin seed, and nettle root, which synergistically combine to help maintain prostrate gland health. In a preferred embodiment of the invention, the dietary supplement includes about 5% to about 25% by weight saw palmetto oil extract, about 12% to about 32% by weight pumpkin seed oil extract, and about 1% to about 21% by weight nettle root extract.

13 Claims, No Drawings

DIETARY SUPPLEMENT CONTAINING SAW PALMETTO, PUMPKIN SEED, AND NETTLE ROOT

CROSS REFERENCE TO RELATED APPPLICATIONS

This application is a continuation-in-part of U.S. patent application Ser. No. 09/137,473 filed Aug. 20, 1998.

BACKGROUND OF THE INVENTION

The present invention relates to a dietary supplement for use in supporting and maintaining normal prostrate gland function. Specifically, the dietary supplement includes an effective amount of saw palmetto extract, pumpkin seed oil extract and nettle root extract.

The use of plants or plant extracts in dietary supplements has long been used to prevent or control disorders of the human body. The prostrate gland is the source of several common disorders for men. These disorders include prostatitis and benign prostatic hyperplasia (BPH). BPH is a condition associated with aging which affects a large percentage of men over the age of fifty. The symptoms associated with BPH are many and varied. These symptoms include frequent, painful urination, an increased need to urinate, a need to urinate often, especially at night, difficulty in starting to urinate, and a weak or interrupted stream of urination, among others.

A number of plants and plant extracts are known for alleviating the symptoms of BPH. U.S. Pat. No. 5,543,146 to Perez describes treatment of BPH with tablet compositions containing both pumpkin seed and saw palmetto extract. A German reference, W. Vahlensieck, Jr., et al., Drug Treatment of Benign Prostatic Hyperplasia, FORTSCHR-MED., Nov. 10, 1996, at 407—11, also teaches the combination of pumpkin seed and saw palmetto. U.S. Pat. No. 4,886,665 to Kovacs describes the use of an oat extract and a nettle extract in a food supplement for the treatment or prevention of various disfunctions of the human body, including BPH.

While a number of plants and plant extracts are known for preventing or treating the symptoms of BPH, none of the known dietary supplements include a comprehensive combination of plant extracts which address many of the symptoms associated with BPH. Consequently, there is a need for a comprehensive combination of plant extracts and phytochemicals which address many of symptoms associated with BPH and therefore, can be beneficial in supporting or maintaining prostrate gland health.

SUMMARY OF THE INVENTION

The present invention provides a comprehensive combination of plant extracts and phytochemicals in a dietary supplement for use in supporting and maintaining normal prostrate gland function. The dietary supplement contains about 5% to about 25% by weight saw palmetto oil extract, about 12% to about 32% by weight pumpkin seed oil extract and about 1% to about 21% by weight nettle root extract. Additionally, the dietary supplement may include Vitamin A and other antioxidants.

All percentages referred to in the specification and appended claims are by weight unless otherwise stated.

DETAILED DESCRIPTION OF THE PREFERRED EMBODIMENTS

This invention is directed to a dietary supplement for use in supporting and maintaining normal prostrate gland function. The dietary supplement of the present invention provides a unique combination of herbal extracts including saw palmetto, pumpkin seed, and nettle root, which synergistically combine to help maintain prostrate gland health. In a preferred embodiment of the invention, the dietary supplement includes about 5% to about 25% by weight saw palmetto oil extract, about 12% to about 32% by weight pumpkin seed oil extract, and about 1 % to about 21% by weight nettle root extract.

The saw palmetto for use in this invention may be derived from the *Serenoa repens* plant species. In general, these plants are fan palms which grow in the South Central and South Eastern regions of the United States. The plant matures to approximately 10 feet with leaf clusters attaining a length of two or more feet. The brownish-black berry is harvested commercially for use in the dietary supplement and pharmaceutical industry. Other common names for saw palmetto include sabal, American Dwarf palm tree, and cabbage palm.

Saw palmetto is available commercially from a number of sources. Commercial extracts of the saw palmetto berry typically contain mostly free fatty acids with smaller amounts of fatty alcohols, and sterols, including β-sitosterol. Preferably, the saw palmetto for use in this invention is extracted from the fruit of the saw palmetto plant. In addition, it is preferred that the saw palmetto extract contains about 80% to about 95% fatty acids.

The pumpkin seed for use in this invention may be derived from various species including, but not limited to, *Cucurbita pepo, Cucurbita maxima, Cucurbita moshata, Cucurbita argyro-sperma*, and *Cucurbita ficifolia*. Preferably, the pumpkin seed used in this invention is derived from the *Cucurbita pepo* species. Pumpkin seed is native to America but is also cultivated worldwide. Imports are available from the former USSR, Yugoslavia, China, Austria, Hungary, and Mexico. Synonymous names include *Semen peponis* (Latin), Kurbissamen (Germany) Graine de pepon, Graine de courge, and Graine de citroulle (France).

In general, pumpkin seeds are greenish to earth colored with a flattened oval shape. Each seed is approximately 7–15 mm long with the micropyle recognizable at the narrow pointed end. Commercial pumpkin seed is primarily obtained from cultivated varieties which do not have a testa. *Cucurbita pepo* is an annual with prostrate shoots up to 10 meters long. The leaves are very large and generally have five distinct lobes. The plant also contains yellow dioecious flowers with a funnel shaped corolla. The seeds are housed within the huge spherical berries of the plant.

Pumpkin seed is available commercially from a number of sources. The constituents in fresh pumpkin seed typically include fixed oils, free fatty acids, steroids, phosphatic acid, fiber, pectins, protein, tocopherols, and trace elements such as phosphorus, potassium, magnesium, calcium, sodium, selenium, manganese, zinc, and copper. The amounts and types of these constituents may be influenced by location, year, variety and location/year interactions. Two types of fatty acids which are found in pumpkin seed include, but are not limited to, Oleic and Linoleic acids. Preferably, the pumpkin seed extract used in this invention includes about 80% to about 95% free fatty acids. Steroids that may be found in pumpkin seed include 24β-ethyl-5α-cholestra-7,25(27)-dien-3β-ol and 24β-ethyl-5 α-cholestra-7-trans22,25(27)-trien-3β-ol. Smaller quantities of sterol glucosides and $\Delta^5$ and $\Delta^8$-sterols are also found in pumpkin seed.

The nettle root for use in this invention may be derived from various species including, but not limited to, *Urtica*

*dioca* and *Urtica urens.* Nettles are plants which are native to Europe and are found in the United States and Canada. These perennials have an erect stalk and can attain a height up to three feet. The dark green serrated leaves grow opposite each other along the stalk. The constituents in nettle include flavonoids, lectins, amines, minerals, and other plant substances such as chlorophylls, carotenoids, vitamins, triterpenes, sterols, and carboxylic acids such as formic and citric acids. Important flavonoids found in nettles include glycosides of quercetin (isoquercitrin and rutin), kaempferol, and isorhamnetin. The amines are usually found in small amounts and include histamine, choline, acetylcholine and serotonin. The amines are primarily found in the stinging bristles of the plant. Important carotenoids found in nettle include β-carotene and xanthophylls. Important sterols found in nettle include β-sitosterol. Preferably, the nettle used in this invention includes about 0.2% to about 1.2% by weight β-sitosterol. In addition, the nettle root extract is preferably provided in a powdered form.

The saw palmetto, pumpkin seed, and nettle may be isolated from their plant sources by any means available. Preferably, these constituents are isolated through solvent extraction. The extract may be further purified through chromatography or other purification methods.

The dietary supplement of the present invention may also include other dietary needs such as vitamins, minerals, antioxidants and other natural elements. Preferably, the dietary supplement of this invention includes one or more sources of Vitamin A. A preferred source of Vitamin A is beta-carotene. Preferably, the beta-carotene used in this invention is derived from natural sources. These natural sources include, but are not limited to *Dunaliella algae* or *Chloroccus algae.*

As used herein, an "antioxidant" includes any compound that is effective in retarding the oxidation of a molecule such as a lipid, lipoprotein, protein or DNA. Suitable antioxidants for us in this invention, in addition to Vitamin A, include, but are not limited to, vitamin C, vitamin E ( -tocopherol), bilberry extract, carotenoids, and lemon bioflavonoids. Suitable carotenoids include, but are not limited to, alpha-carotene, gamma carotene, lycopene, zeaxanthin, capsanthin, and lutein., The dietary supplement of the present invention may also include one or more excipients, such as carriers and/or binders for use in providing a dietary supplement product in a consumable form. Preferably, the dietary supplement of this invention is ingested orally, but other consumable forms may be appropriate. Carriers and binders are known to those skilled in the art and are typically neutral, non-toxic, additives that facilitate consumption and absorption of the product by the user. Examples of liquid carriers include vegetable oils, such as corn and soybean oils, and mineral oils. Examples of solid carriers and binders include yellow bees wax, glucose, sucrose, starch, lactose, mannitol, magnesium stearate, magnesium carbonate, talcum, and cellulose. Preferably, the binders and carriers are derived from natural sources. In the present invention, the binders and carriers include yellow beeswax, glycerin and soybean oil.

The dietary supplement of the present invention is preferably provided as a unit dosage in a softgel capsule. Typically, a softgel capsule is made from gelatin, but other proteins or compounds may also be used. Suitable softgel capsules are available from R. P. Scherer, St. Petersburg, Fla.

The amounts of saw palmetto, pumpkin seed, nettle, and the other phytochemicals may be varied to provide the desired unit dosage and/or desired affect. The unique combination of saw palmetto, pumpkin seed and nettle root extracts synergistically combine to support normal prostrate gland function and normal urinary flow.

In a preferred embodiment of the invention, the dietary supplement includes the ingredients shown in Table 1.

TABLE 1

| Ingredient | amount (wt %) |
|---|---|
| Pumpkin seed oil extract | 23.50 |
| Saw Palmetto oil extract | 15.67 |
| Nettle Root powdered extract | 11.75 |
| Gelatin | 19.25 |
| Beta carotene, 2.15% | 0.98 |
| Lemon Bioflavonoids complex | 4.89 |
| Excipients | 23.96 |
| Total | 100.00 |

In yet another embodiment of this invention, one or more unit dosages of the dietary supplement provides the daily nutritional needs as shown in Table 2:

TABLE 2

| Ingredient | amount |
|---|---|
| Pumpkin seed oil extract | 480 mg |
| Saw Palmetto oil extract | 320 mg |
| Nettle Root powdered extract | 240 mg |
| Beta carotene | 300 IU or 6% of the RDI for Vitamin A |
| Lemon Bioflavonoids complex | 100 mg |

Preferably three softgels are used to provide the daily nutritional needs as shown in Table 2. Accordingly, the amount of each ingredient found in a single capsule is shown in Table 3 below:

TABLE 3

| Ingredient | amount |
|---|---|
| Pumpkin seed oil extract | 160 mg |
| Saw Palmetto oil extract | 107 mg |
| Nettle Root powdered extract | 80 mg |
| Betacarotene | 2% of the RDI for Vitamin A |
| Lemon Bioflavonoids complex | 33.3 mg |

The dietary supplement as described above may be used in a method for supporting and maintaining normal prostrate gland function. In a preferred embodiment, the method comprises the step of consuming an oral dietary supplement comprising by weight about 5% to about 25% saw palmetto oil extract, about 12% to about 32% pumpkin seed oil extract, about 1 % to about 21% nettle root extract, and excipients, wherein the amount of ingredients in the dietary supplement totals 100%. In another embodiment of the invention, the dietary supplement is consumed orally twice per day. In yet a further embodiment, the dietary supplement is consumed orally three times per day.

The following example presents the results of a clinical study conducted to measure the effects of dietary supplementation with a saw palmetto, nettle root, and pumpkin seed supplement in accordance with the present invention.

EXAMPLE 1

44 men having an average age of 64 years and an average IPSS symptom score of 18 participated in a six-month, double-blind study. The participants were randomized to either a placebo or to a supplement containing saw palmetto, nettle root, and pumpkin seed extracts. A one-month, single-blind placebo lead-in preceded the double-blind study. The participants receiving the dietary supplementation received 320 mg/day of saw palmetto extract, 240 mg/day of nettle root extract, and 480 mg/day of pumpkin seed extract. Prostrate gland MRI and ultrasound-guided biopsy for tissue study, conducted at baseline and after six months, was available on 41 participants.

The 82 tissue samples were batch-studied by a series of tests, including routine histology, morphometry, immunohistochemical assessment, and tissue homogenate radioimmunoassay. A contraction in the transition zone epithelium, from 17.8% before supplementation to 10.7 % after six months of supplementation, was found in the participants receiving the saw palmetto, nettle root, and pumpkin seed extracts supplement. In addition, the participants receiving the saw palmetto blend supplement experienced an increase in their epithelial atrophy score. The average score increased form 25.2% before supplementation to 40.9% after six months of supplementation. In contrast, no significant changes in tissue measurements were seen in the participants receiving the placebo.

It should be understood that a wide range of changes and modifications may be made to the embodiments described above. It is intended, therefore, that the foregoing description illustrates rather than limits this invention, and that it is the following claim, including all equivalents, that define this invention.

What is claimed:

1. A dietary supplement for supporting and maintaining normal prostate gland function, said supplement comprising by weight:
    a. about 15.67% by weight saw palmetto oil extract;
    b. about 23.5% by weight pumpkin seed oil extract;
    c. about 11.75% by weight powdered nettle root;
    d. excipients, wherein the amount of ingredients in said dietary supplement totals 100%, whereby the combination of the saw palmetto oil extract, pumpkin seed oil extract, and powdered nettle root is effective to cause prostate epithelial contraction in a mammal who ingests said dietary supplement.

2. The dietary supplement of claim 1 further comprising about 0.1% to about 10% by weight of Vitamin A.

3. The dietary supplement of claim 2 further comprising about 0.1% to about 10% by weight of an antioxidant.

4. The dietary supplement of claim 2 wherein said Vitamin A is derived from Beta carotene.

5. The dietary supplement of claim 1 wherein said saw palmetto extract, said pumpkin seed extract, said nettle root extract, and said excipients are provided in a single capsule suitable for oral ingestion.

6. The dietary supplement of claim 4 wherein said saw palmetto extract, said pumpkin seed extract, said nettle root extract, said excipients, and said beta carotene are provided in a single capsule suitable for oral ingestion.

7. The dietary supplement of claim 6 wherein each capsule provides about 107 mg of saw palmetto extract, about 80 mg of nettle root extract, about 160 mg of pumpkin seed oil, and about 2% of the recommended daily intake (RDI) of Vitamin A.

8. The dietary supplement of claim 4 wherein said beta carotene is derived from algae of the genera Dunaliella or Chloroccus.

9. A method for supporting and maintaining normal prostrate gland function, said method comprising the step of:
    a. consuming an oral dietary supplement comprising by weight about 15.67% saw palmetto oil extract, about 23.5% pumpkin seed oil extract, about 11.75% powdered nettle root, and excipients, wherein the amount of ingredients in said dietary supplement totals 100%, whereby the combination of the saw palmetto oil extract, pumpkin seed oil extract, and powdered nettle root is effective to cause prostate epithelial contraction in a mammal who ingests said dietary supplement.

10. The method of claim 9 wherein said dietary supplement further comprises about 1% by weight of Vitamin A.

11. The method of claim 10 wherein said dietary supplement provides about about 107 mg of saw palmetto extract, about 80 mg of nettle root extract, about 160 mg of pumpkin seed oil, and about 2% of the recommended daily intake (RDI) of Vitamin A.

12. The method of claim 11 wherein said dietary supplement is consumed orally twice per day.

13. The method of claim 11 wherein said dietary supplement is consumed orally three times per day.

* * * * *